(12) United States Patent
Asif et al.

(10) Patent No.: US 11,751,800 B2
(45) Date of Patent: Sep. 12, 2023

(54) SEIZURE DETECTION USING CONTEXTUAL MOTION

(71) Applicant: INTERNATIONAL BUSINESS MACHINES CORPORATION, Armonk, NY (US)

(72) Inventors: Umar Asif, Melbourne (AU); Stefan von Cavallar, Sandringham (AU); Jianbin Tang, Doncaster East (AU); Stefan Harrer, Hampton (AU)

(73) Assignee: International Business Machines Corporation, Armonk, NY (US)

( * ) Notice: Subject to any disclaimer, the term of this patent is extended or adjusted under 35 U.S.C. 154(b) by 442 days.

(21) Appl. No.: 17/077,020

(22) Filed: Oct. 22, 2020

(65) Prior Publication Data
US 2022/0125370 A1 Apr. 28, 2022

(51) Int. Cl.
*A61B 5/00* (2006.01)
*G16H 50/70* (2018.01)
(Continued)

(52) U.S. Cl.
CPC .......... *A61B 5/4094* (2013.01); *A61B 5/7267* (2013.01); *G06T 7/00* (2013.01);
(Continued)

(58) Field of Classification Search
CPC ... A61B 5/4094; A61B 5/7267; A61B 5/1113; G06T 7/00; G06T 7/20; G06T 7/70;
(Continued)

(56) References Cited

U.S. PATENT DOCUMENTS 9,864,912 B2   1/2018 Min
10,388,016 B2  8/2019 Kusens
(Continued)

FOREIGN PATENT DOCUMENTS

WO   2017032775 A1   3/2017

OTHER PUBLICATIONS

Asif et al., "Privacy Preserving Human Fall Detection using Video Data." Proceedings of the Machine Learning for Health NeurIPS Workshop, in PMLR 116:39-51, 2020, pp. 1-13.
(Continued)

*Primary Examiner* — Md K Talukder
(74) *Attorney, Agent, or Firm* — Anthony Curro

(57) ABSTRACT

A method, a computer program product, and a computer system determine abnormal motion from a patient. The method includes receiving sensory data of the patient and a location in which the patient is present. The sensory data includes video data over a period of time the patient is being monitored. The method includes generating contextual information based on the sensory data. The contextual information is indicative of surroundings of the patient and characteristics of the location. The method includes generating motion information based on the sensory data. The motion information is indicative of movement of the patient in the location. The method includes generating contextual motion data by incorporating the contextual information with the motion information. The method includes determining the abnormal motion based on the contextual motion data.

17 Claims, 5 Drawing Sheets

(51) Int. Cl.
*G06T 7/00* (2017.01)
*G06T 7/20* (2017.01)
*G06T 7/70* (2017.01)

(52) U.S. Cl.
CPC ............... *G06T 7/20* (2013.01); *G06T 7/70* (2017.01); *G16H 50/70* (2018.01)

(58) Field of Classification Search
CPC ........ G16H 50/70; G16H 30/40; G16H 50/20; G16H 50/50
See application file for complete search history.

(56) References Cited

U.S. PATENT DOCUMENTS

| | | | |
|---|---|---|---|
| 10,417,775 B2 | 9/2019 | Wang | |
| 2006/0110049 A1 | 5/2006 | Liang | |
| 2009/0062696 A1* | 3/2009 | Nathan | A61B 5/7282 600/595 |
| 2011/0263946 A1* | 10/2011 | el Kaliouby | A61B 5/16 600/300 |
| 2013/0060167 A1* | 3/2013 | Dracup | A61B 5/11 600/595 |
| 2014/0350436 A1* | 11/2014 | Nathan | A61B 5/7282 600/595 |
| 2015/0157242 A1 | 6/2015 | Sabesan | |
| 2015/0164377 A1 | 6/2015 | Nathan | |
| 2015/0213323 A1 | 7/2015 | Bala | |
| 2017/0185830 A1* | 6/2017 | Srivastava | G06F 3/017 |
| 2019/0261065 A1 | 8/2019 | Lokshin | |
| 2019/0279046 A1 | 9/2019 | Han | |
| 2019/0336061 A1 | 11/2019 | Harrer | |
| 2022/0125370 A1* | 4/2022 | Asif | G06T 7/70 |

OTHER PUBLICATIONS

Asif et al., "SeizureNet: Multi-Spectral Deep Feature Learning for Seizure Type Classification," [Submitted on Mar. 8, 2019 (v1), last revised Apr. 2, 2020 (this version, v4)], https://arxiv.org/abs/1903.03232, pp. 1-10.

Asif, "SSHFD: Single Shot Human Fall Detection with Occluded Joints Resilience," [Submitted on Apr. 2, 2020 (v1), last revised Apr. 3, 2020 (this version, v2)], https://arxiv.org/abs/2004.00797 ages 1-8.

Mell et al., "The NIST Definition of Cloud Computing", National Institute of Standards and Technology, Special Publication 800-145, Sep. 2011, pp. 1-7.

Roy et al., "Deep Learning Enabled Automatic Abnormal EEG Identification," 2018 40th Annual International Conference of the IEEE Engineering in Medicine and Biology Society (EMBC), Honolulu, HI, pp. 2756-2759, 2018.

Roy et al., "Machine Learning for Seizure Type Classification: Setting the benchmark," https://arxiv.org/abs/1902.01012, Feb. 4, 2019, pp. 1-5.

* cited by examiner

SEIZURE DETECTION USING CONTEXTUAL MOTION

BACKGROUND

The exemplary embodiments relate generally to seizure detection, and more particularly to generating and utilizing contextual motion data based on contextual information and motion information to determine when a seizure event occurs.

Epilepsy monitoring units (EMUs) may provide patients with epilepsy care by specialists to diagnose and/or treat epilepsy or seizures. The patient may receive care from the EMU as an inpatient (e.g., while in a center run by the EMU) or outpatient (e.g., while remote to a central EMU location such as the patient's home). In receiving the care from the EMU, the patient may provide real-world video data including the patient that may be monitored manually or using automated systems to detect when the patient has an epileptic episode or suffers from a seizure.

When the automated system is used to detect when a seizure or epileptic episode is occurring, the automated system may utilize various detection techniques. However, conventional approaches often utilize motion data exclusively to detect a seizure or epileptic episode.

U.S. Publ. Appln. No. 2019/0336061 describes a conventional approach using deep learning methods. Motion from patients are monitored and measured with measurement devices that generate input signals. The input signals are run through classification models that are weighted so that a result from considering the classification models indicates whether an epilepsy seizure has occurred. This conventional approach relies on motion data alone through a plurality of models that is weighted to improve accuracy. In a substantially similar manner, U.S. Publ. Appln. No. 2015/0157242 describes a motion-based seizure detection system that obtains and analyzes motion data using an accelerometer or an image-capture device to acquire the subject motion data. As the onset of a seizure often includes changes in movement, this conventional approach determines position information, orientation information, or posture information of the subject through the motion data. Again, this conventional approach only relies on motion data of the subject. Further conventional approaches in detecting a seizure or abnormal motion such as U.S. Publ. Appln. No. 2015/0164377 and U.S. Publ. Appln. No. 2014/0350436 also rely only on motion data. However, the motion data as used in these conventional approaches is only indicative of how a patient is moving without incorporation of other non-motion information.

When non-motion information is used, the conventional approach still does not provide an enriched data set to detect seizures or epileptic episodes. For example, "Deep Learning Enabled Automatic Abnormal EEG Identification" to Roy et al. describes abnormal EEF signals as an input for deep neural networks that purportedly provide meaningful representations that may be used for brain-related disorders such as epilepsy. However, this conventional approach does not describe any use of video data analytics, utilizing alternate representations of video data for action classification, or the use of contextual information for video analysis.

Other conventional approaches directed toward seizure detection and/or epilepsy related episodes provide features that may be used. For example, "Privacy Preserving Human Fall Detection using Video Data" to Asif et al. and "SeizureNet: Multi-Spectral Deep Feature Learning for Seizure Type Classification" to Asif et al. describe utilizing de-identified data. However, with the focus on how data may be de-identified, these conventional approaches do not describe the information that is used in detecting a seizure.

SUMMARY

The exemplary embodiments disclose a method, a computer program product, and a computer system for determining abnormal motion from a patient. The method comprises receiving sensory data of the patient and a location in which the patient is present. The sensory data includes video data over a period of time the patient is being monitored. The method comprises generating contextual information based on the sensory data. The contextual information is indicative of surroundings of the patient and characteristics of the location. The method comprises generating motion information based on the sensory data. The motion information is indicative of movement of the patient in the location. The method comprises generating contextual motion data by incorporating the contextual information with the motion information. The method comprises determining the abnormal motion based on the contextual motion data.

In a preferred embodiment, the contextual motion data is generated synthetically by generating a virtual environment based on the contextual information, generating a model actor representing the patient, generating a simulation of the movement of the patient via the model actor in the virtual environment, and processing the simulation.

In a preferred embodiment, the virtual environment and the model actor de-identifies the location and the patient, respectively.

In a preferred embodiment, the abnormal motion is determined according to a model trained with historical seizure events, the historical seizure events including respective historical contextual motion data.

In a preferred embodiment, the method further comprises validating the abnormal motion and updating the model with the contextual motion data.

In a preferred embodiment, the historical seizure events are from the patient and further patients and from the location and further locations.

In a preferred embodiment, the sensory data further includes electroencephalogram (EEG) data of the patient corresponding to when the movement occurs.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
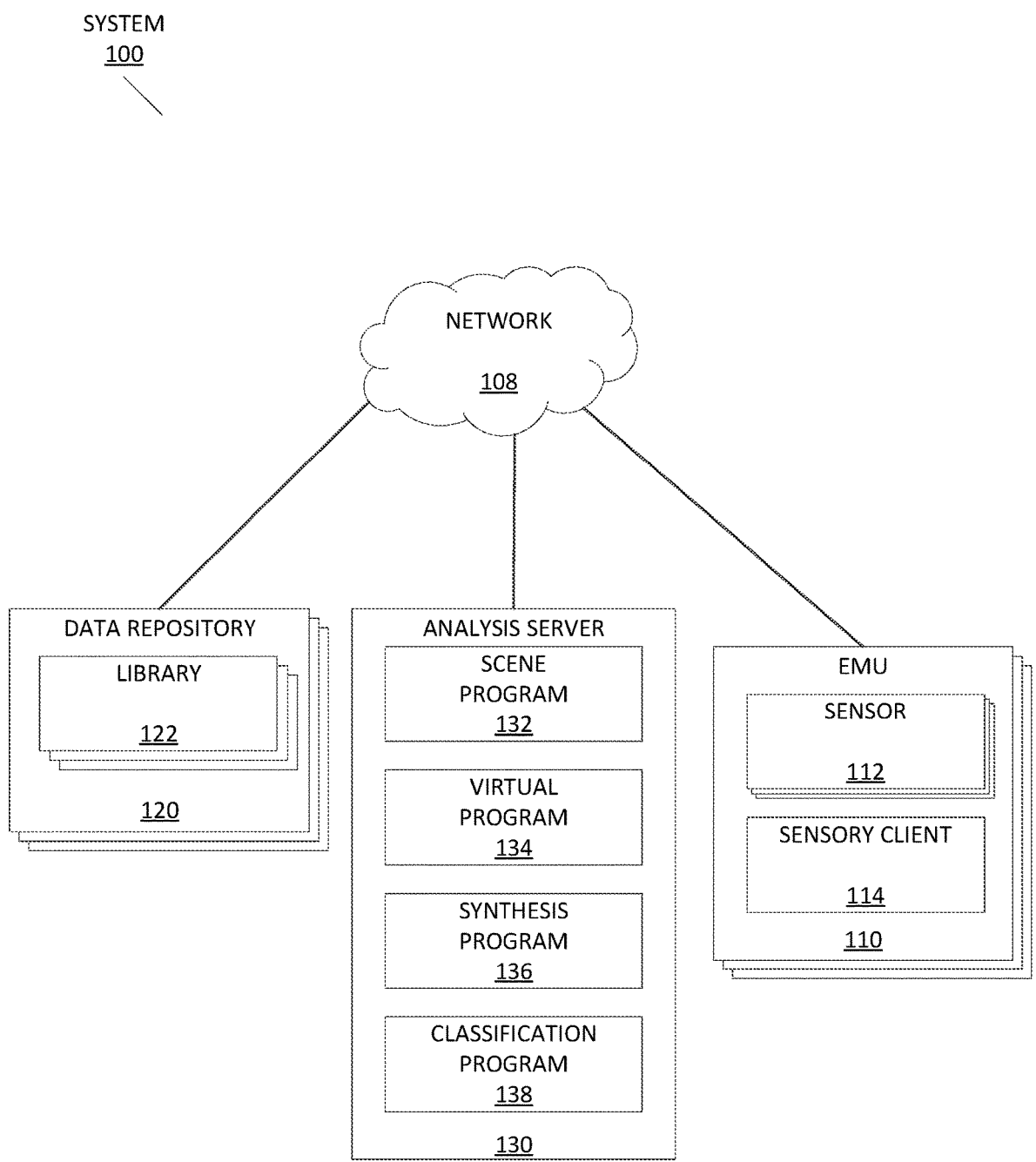
FIG. 1 depicts an exemplary schematic diagram of an motion detection system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

The exemplary embodiments are directed to a method, computer program product, and system for detecting seizures based on real-world video data from epilepsy monitoring units (EMUs). As will be described in greater detail herein, the exemplary embodiments are configured to abnormal motion from a patient using contextual motion data that is synthesized from motion information and contextual information. The exemplary embodiments provide a mechanism to generate the contextual motion data synthetically by simulating movement based on the motion information in a virtual environment created based on the contextual information. Key benefits of the exemplary embodiments may include providing a mechanism to detect seizures with increased accuracy via the contextual motion data that is richer and more discriminative, preserving privacy by de-identifying the motion and contextual information, and maintaining a source in which subsequent motion may be processed to determine instances of abnormal motion that has improved classification accuracy. Detailed implementation of the exemplary embodiments follows.

The exemplary embodiments are described with regard to detecting seizures based on real-world video data provided by EMUs that is de-identified. However, the exemplary embodiments may be utilized and/or modified for various other purposes using any available data. For example, the detection of epileptic seizures is only used for illustrative purposes. In another exemplary implementation, the exemplary embodiments may be configured to detect other types of seizures (e.g., caused by brain disorders or other reasons) or abnormal motion in a general matter where the abnormal motion may be indicative of the patient experiencing involuntary movement, movement that may result in injury, movement indicative of an underlying condition, etc. In another example, the data from EMUs is only used for illustrative purposes. In another exemplary implementation, the exemplary embodiments may have access to sensory data (e.g., from devices carried on a patient), other video data (e.g., security or closed circuit feeds), etc. In this manner, the exemplary embodiments may provide detection of motion related events with increased accuracy while preserving privacy of patients being monitored.

FIG. 1 depicts a motion detection system 100, in accordance with the exemplary embodiments. According to the exemplary embodiments, the motion detection system 100 may include one or more EMUs 110, one or more data repositories 120, and an analysis server 130, which may all be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the network 108 may be a communication channel capable of transferring data between connected devices. Accordingly, the components of the motion detection system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a WiFi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices. For example, the network 108 may also represent direct or indirect wired or wireless connections between the components of the motion detection system 100 that do not utilize the network 108.

In the exemplary embodiments, the EMU 110 may represent any location with sensory components in which a patient may be monitored to detect when a seizure occurs from determining abnormal motion associated with the patient. For example, the EMU 110 may be an inpatient location in which the patient arrives at a center of the EMU 110 and receive treatment and/or monitoring. In another example, the EMU 110 may be an outpatient location in which the patient remains at a remote location. At the remote location, specialists may treat the patient, provide monitoring services, etc. In each EMU 110, there may be one or more sensors 112 and a sensory client 114 which may be embodied in an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an Internet of Things (IoT) device, or any other electronic device or computing system capable of receiving and sending data to and from other computing devices. The components utilized in the EMUs 110 may be individual components, comprised of a cluster or plurality of computing devices, in a modular manner, etc., working together or working independently. The components of the EMU 110 are described in greater detail as a hardware implementation with reference to FIG. 3, as part of a cloud implementation with reference to FIG. 4, and/or as utilizing functional abstraction layers for processing with reference to FIG. 5.

In the exemplary embodiments, the sensors 112 may be any device that is capable of monitoring the patient and generate corresponding sensory data. For example and as utilized in accordance with the exemplary embodiments, the sensors 112 may include an imager that captures images of the location of the EMU 110 where the patient is located to generate video information. The imagers may generate real-world video data that show the patient location in a local manner (e.g., within the location of the EMU 110) and surrounding objects (e.g., medical equipment, furniture, randomly placed materials, etc.) that are within a field of the view of the imager. To capture real-world video data within confines of the location of the EMU 110, the sensors 112 may include a plurality of imagers such that the entire volume of the location may be visualized as well as eliminating or minimizing occlusion of the objects inside the location. For example, the imagers may be at fixed positions at strategically placed locations to achieve the above noted features for the real-world video data. In another example, the imagers may alternatively or additionally be dynamically positioned to be moved (e.g., along any translational or rotational axis) or otherwise modify the field of view of the imagers (e.g., zooming in or out) to achieve the above noted features for the real-world video data.

The sensors 112 may include further devices that provide corresponding sensory data. For example, the sensors 112 may include an electroencephalogram (EEG) device to monitor electrical activity on the patient's brain. Through a device worn by the patient, the EEG information may be monitored and corresponding sensory data may be generated. In another example, the sensors 112 may include an audio input device to monitor audio activity that may occur in the location of the EMU 110. In a similar manner to the imagers, the sensors 112 may include a plurality of audio input devices to capture sounds occurring within a volume of the location of the EMU 110. The audio information may provide redundant indications and/or allow for confirmation of determinations based on the video information. In a further example, the sensors 112 may include motion monitoring devices (e.g., an accelerometer) that may be local on the patient to determine motion being experienced by the patient and generate corresponding motion related information. In yet another example, the sensors 112 may include location determining devices (e.g., global positioning system (GPS) devices) that may be used in determining location and/or movement related sensory data. The location determining devices may additionally be used to correlate information with the respective EMU 110. As those skilled in the art will understand, the EMU 110 may utilize any number and type of the sensors 112 to provide different types of information that may be used, particularly with regard to the features of the exemplary embodiments.

In the exemplary embodiments, the sensory client 114 may act as a client in a client-server relationship and may be a software, hardware, and/or firmware based application capable of exchanging sensory data via the network 108. In embodiments, the sensory client 114 may operate in a background capacity (e.g., relative to the patient) where sensory data generated by the sensors 112 are exchanged with one or more components of the motion detection system 100, and utilize various wired and/or wireless connection protocols for data transmission and exchange associated with joining the meeting, including Bluetooth, 2.4 gHz and 5 gHz internet, near-field communication, Z-Wave, Zigbee, etc.

In the exemplary embodiments, the data repository 120 may include one or more libraries 122 and may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of storing, receiving, and sending data to and from other computing devices. While the data repository 120 is shown as a single device, in other embodiments, the data repository 120 may be comprised of a cluster or plurality of electronic devices, in a modular manner, etc., working together or working independently. While the data repository 120 is also shown as a separate component, in other embodiments, the data repository 120 may be incorporated with one or more of the other components of the motion detection system 100. For example, the data repository 120 may be incorporated in the analysis server 130. Thus, access to the data repository 120 by the analysis server 130 may be performed locally. The data repository 120 is described in greater detail as a hardware implementation with reference to FIG. 3, as part of a cloud implementation with reference to FIG. 4, and/or as utilizing functional abstraction layers for processing with reference to FIG. 5.

In the exemplary embodiments, the libraries 122 may include databases including historical analyses of contextual motion data and corresponding events. As a seizure event is registered and contextual motion data is generated for the seizure event, the libraries 122 may be used to train models that are used in detecting subsequent seizure events. For example, the incorporation of a historical seizure event and the corresponding contextual motion data may be included in the libraries 122 with validation information. The validation information may indicate whether the contextual motion data results in a true positive, a true negative, a false positive, or a false negative. The validation information may be provided in a manual process in which a specialist of the EMU 110 provides manual inputs during and/or after the seizure event that provides steps taken, results measured, etc. With an increased number of entries included in the libraries 122, the exemplary embodiments may further train the models used in the motion classifier that detects abnormal motion and learn probabilistic distributions about seizure and no-seizure classes. As will be described below, with the information being de-identified, the libraries 122 may be maintained to incorporate historical seizure events and corresponding contextual motion data independent of the patient associated with the seizure event. In this manner, the libraries 122 may provide more robust data to be used in training and learning purposes for subsequent detection of seizures linked with abnormal motion.

In the exemplary embodiments, the analysis server 130 may include a scene program 132, a virtual program 134, a synthesis program 136, and a classification program 138, and act as a server in a client-server relationship with the sensory client 114 as well as be in a communicative relationship with the data repository 120. The analysis server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the analysis server 130 is shown as a single device, in other embodiments, the analysis server 130 may be comprised of a cluster or plurality of computing devices, working together or working independently. The analysis server 130 is described in greater detail as a hardware implementation with reference to FIG. 3, as part of a cloud implementation with reference to FIG. 4, and/or as utilizing functional abstraction layers for processing with reference to FIG. 5.

In the exemplary embodiments, the scene program 132 may be a software, hardware, and/or firmware application configured to generate components parts used in subsequent operations to generate the contextual motion data. Specifically, the scene program 132 may receive sensory data from the EMU 110 to generate contextual information of the setting in which the patient is located and motion information of the patient. Further sensory data such as EEG information, audio information, etc. may also be received that may be used to corroborate or provide additional information in generating the contextual information and/or the motion information.

According to an exemplary embodiment, the scene program 132 may be an AI-based scene analyzer that generates the contextual information. The contextual information may include scene identification (e.g., EMU 110), scene layout (e.g., identification of room floor, wall, ceiling, furniture, etc. along with corresponding positioning in the location of the patient), objects of interests (e.g., patient bed, clinical apparatus, EEG device, etc.), etc. The scene program 132 may also generate the motion information. The motion information may include patterns extracted from time-series EEG data, human pose patterns detected from video data, information such as velocity, intensity, frequency, etc., as well as other types of motion related information for movements of the patient on a time-scale (e.g., temporal data). Therefore, the motion information may indicate movement that the patient exhibits over a period of time. The motion information may also pertain to changes in positioning of non-patient movement (e.g., other individuals, objects, etc.) in the location of the EMU 110. Accordingly, through the above noted operations, the scene program 132 may utilize contextual models (e.g., object recognition (Mask-RCNN), scene classification, room layout detection, etc.) to extract contextual information, and may also utilize motion models (e.g., human-pose estimation, human segmentation, etc.) to generate the motion information.

In the exemplary embodiments, the virtual program 134 may be a software, hardware, and/or firmware application configured to process the contextual information to generate a virtual environment. In generating the virtual environment, the virtual program 134 may filter the contextual information by determining whether an object is relevant to the detection of a seizure. In this manner, the virtual program 134 may analyze the contextual information to generate the virtual environment resembling the real-world environment of the location of the EMU 110 but containing only information of interest (e.g., patient bed, room layout, etc.). In an exemplary implementation, the virtual program 134 may be a GAN-based AI model that mimics real-world textures on the virtual environment. In generating the virtual environment, the virtual program 134 may generate a three dimensional mask representing each object to be included in the virtual environment. In determining which objects in the contextual information are to be included, the virtual program 134 may generate a relevance score indicative of a confidence to be applicable to detecting a seizure event. For each object having a relevance score that satisfies a relevance threshold, these objects may be included in generating the virtual environment. For example, a large piece of furniture (e.g., a patient bed, an armchair, a dresser, etc.) may have a relatively high relevance score that satisfies the relevance threshold. In another example, small items placed on furniture (e.g., a desk lamp, a newspaper, etc.) may have a relatively low relevance score that does not satisfy the relevance threshold. The virtual program 134 may generate the virtual environment to further simulate select characteristics of the objects that are to be included. For example, a relative density of an object may be incorporated in the virtual environment (e.g., a bedframe may be represented with a dense characteristic while a mattress may be represented with a soft characteristic, a furniture made of wood may be represented with a dense characteristic, select portions of a chair may be represented with respective dense and soft characteristics, etc.). Such a feature may hold utility when the abnormal motion is detected and determined to potentially cause injury to the patient (e.g., an inadvertent fall toward a hardwood floor may cause harm to the patient while an inadvertent fall onto a mattress may not cause significant harm to the patient).

The virtual program 134 may also be configured to de-identify the contextual information. For example, the virtual program 134 may generate the mask without any identifying markers that may be used in identifying the location of the EMU 110 and/or the patient at the location of the EMU 110. In another example, the virtual program 134 may generate a mask for the patient in the virtual environment. However, the mask for the patient may be a generalized representation of the patient as an individual such that the patient's identity is removed in the virtual environment.

In the exemplary embodiments, the synthesis program 136 may be a software, hardware, and/or firmware application configured to receive the virtual environment and incorporate the motion information, particularly motion exhibited by the patient in the real-world data. The synthesis program 136 may utilize synthetic data curation techniques (e.g., blender, represent the patient as a three-dimensional mask, etc.) to simulate the motion information on the mask representing the patient in the virtual environment. The synthesis program 136 may determine contextual motion data based on the synthesis of the motion information (e.g., how the patient moves) in the contextual information (e.g., via the virtual environment). In this manner, the synthesis program 136 may output the contextual motion data that enriches the motion information with the contextual information.

In the exemplary embodiments, the classification program 138 may be a software, hardware, and/or firmware application configured to receive the contextual motion data and detect whether the patient has had an abnormal motion. The classification program 138 may include a motion classifier that is fed the contextual motion data that discriminates between normal and abnormal motions (e.g., does a detected motion classify as a seizure event or a no-seizure event). The classification program 138 may utilize various models that are generated based on available information in the libraries 122 to detect when a motion is classified as abnormal. Those skilled in the art will recognize the various manners in which models may be used for event detection that may incorporate the use of various AI techniques and/or neural networks. As a result of the classification program 138 detecting an abnormal motion, the classification program 138 may output an alert to be transmitted to the EMU 110 so that a specialist of the EMU 110 may take appropriate action.

The classification program 138 may also be configured to update and maintain the libraries 122 as contextual motion data is generated with subsequent information that provides hindsight information. For example, a specialist may provide information after the contextual motion data has been generated such as whether the contextual motion data indeed related to a seizure event that may indicate a true positive, a true negative, a false positive, or a false negative. Thus, upon validation of a seizure from clinical staff of the EMU 110 and/or records of the patient (e.g., an EHR), the classification program 138 may analyze the classifier decisions for the contextual motion data. The classification program 138 may associate the results of the analysis with the contextual motion data, the contextual information, and the motion information which may then be stored in the libraries 122. The libraries 122 may also store the various models that are used in detecting whether a motion is normal or abnormal. The classification program 138 may update the models using the additional information that is now available through model improvements using online-training. Based on the motion classifier of the classification program 138, the classification program 138 may utilize a deep CNN model with two-neurons layer configuration to learn probabilistic distributions about seizure and no-seizure classes.

The exemplary embodiments utilize contextual motion data that is a representation of de-identified information extracted from human pose characteristics, movement patterns, and task-relevant information extracted from the environment or location that is being monitored. The contextual motion data may be generated synthetically using cues from real-world data. The contextual motion data may minimize noise and variations in the real-world data and enable AI methods to successfully generalize to different real-world environments involving different people, which are critical requirements for AI-based solutions in health informatics.

Through the contextual motion data generated using the operations performed by the analysis server 130, the exemplary embodiments may preserve patient privacy which is critical in health information. The exemplary embodiments may de-identify video data into motion characteristics such as human pose patterns, human segmentation masks, and information such as velocity, intensity, and frequency of movements on time-scale (i.e., temporal data). The exemplary embodiments further utilize the contextual motion data that richer and more discriminative compared to raw motion information. Due to the contextual motion data replicating a patient's motion patterns in a virtual environment, the contextual motion data may be invariant to human physical appearances and background information (e.g., the location of the EMU 110). The classifier may therefore generalize seizure detection in new environments and different patients which are critical requirements in health informatics. The exemplary embodiments further maintain an online library containing contextual motion data for validated seizure occurrences. The library samples may therefore be used to re-train the AI model for improved classification accuracy. The library may also be considered an important data asset containing de-identified transformation of real-world sensitive hospital or EMU data that may be extended and shared among multiple locations for advancing epilepsy research and promoting crowd-sourced AI challenges.

Figure 2:
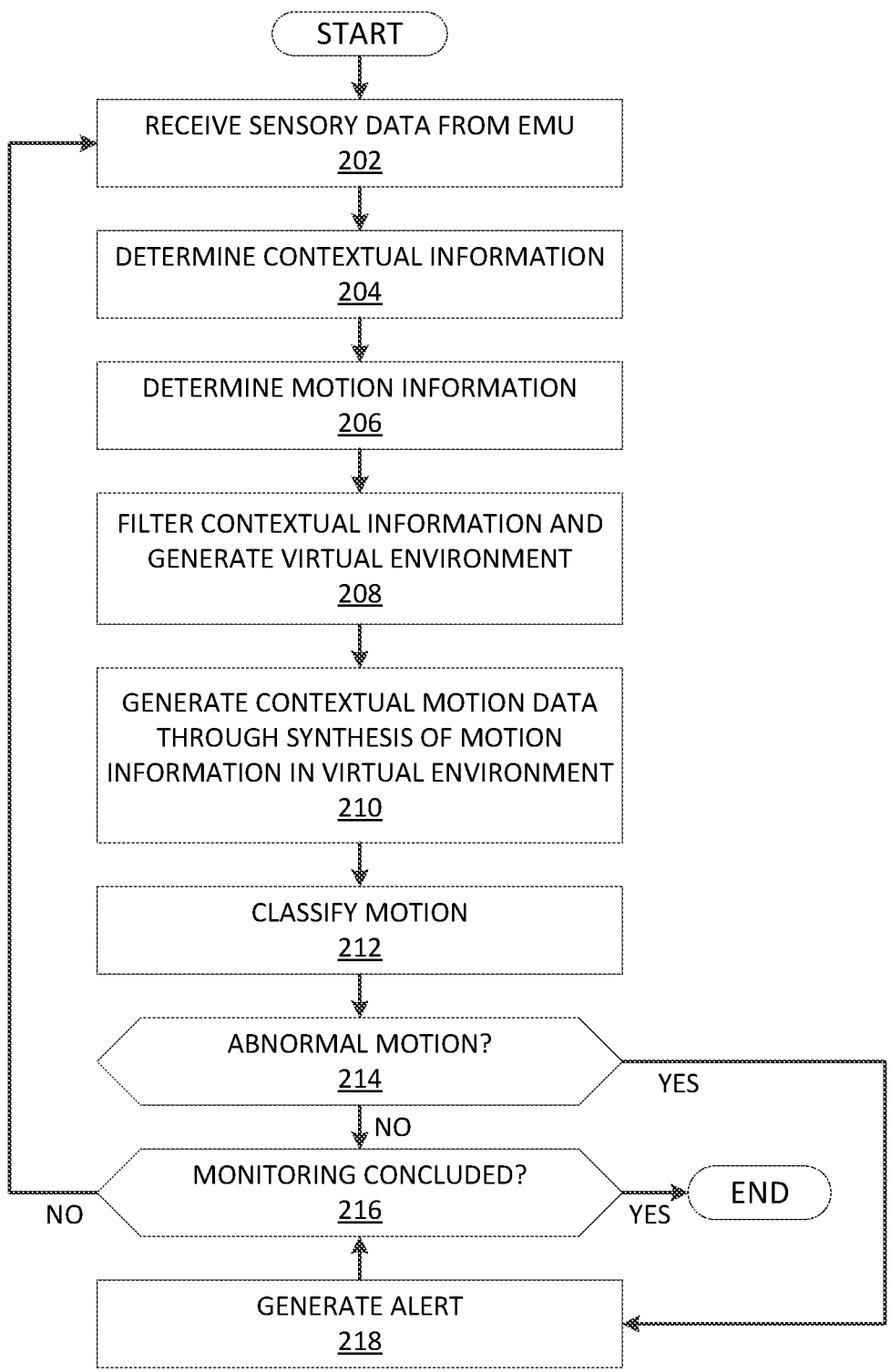
FIG. 2 depicts an exemplary flowchart of a method illustrating the operations of an analysis server 130 of the motion detection system 100 in determining an abnormal motion event, in accordance with the exemplary embodiments.

FIG. 2 illustrates an exemplary flowchart of a method 200 illustrating the operations of the analysis server 130 of the motion detection system 100 in determining an abnormal motion event, in accordance with the exemplary embodiments. The method 200 is described with regard to operations performed by the scene program 132, the virtual program 134, the synthesis program 136, and the classification program 138 of the analysis server 130. Accordingly, the method 200 is described from the perspective of the analysis server 130.

The analysis server 130 may receive sensory data from the EMU 110 (step 202). As described above, the EMU 110 may represent a location in which the patient is present. The EMU 110 may also include the sensors 112 that generates corresponding sensory data based on the type of sensor being used. Among the sensors 112, the EMU 110 may include one or more imagers that capture video data (e.g., real-world video data) where a field of view includes the patient and the surroundings of the patient (e.g., up to dimensions of an enclosed room such as a hospital room). In generating the sensory data by the sensors 112, the sensory client 114 may transmit the sensory data to the analysis server 130.

Using the sensory data, the analysis server 130 may determine contextual information (step 204). The contextual information may be indicative of the surroundings of the location where the patient is present. The surroundings may relate to objects that are within the location where the patient is present (e.g., patient bed, medical equipment, other furniture, items dispersed around the room, etc.). The surroundings may also relate to characteristics of the location where the patient is present (e.g., walls, doors, dimensions, etc.).

Using the sensory data, the analysis server 130 may also determine motion information (step 206). The motion information may be indicative of movement being exhibited by the patient over a period of time (e.g., within a monitoring window from start to end, within a portion of the monitoring window when a potential seizure event is registered, etc.). The patient may move voluntarily or involuntarily in a normal or abnormal manner. The sensory data may capture changes in the position, orientation, configuration, etc. of the patient over the period of time. The analysis server 130 may identify the changes associated with movement to determine when and how the patient is moving.

The analysis server 130 may filter the contextual information and may generate a virtual environment based on the filtered contextual information (step 208). In preparation to generate the virtual environment, the analysis server 130 may determine select aspects of the contextual information that is to be included in the virtual environment based on a relevance to detect abnormal motion exhibited by the patient. For example, a relatively large object (e.g., furniture) may have a greater relevance than a small item such as one that is only temporarily placed within the location (e.g., a lunch bag, a newspaper, etc.). In another example, characteristics of the location may have a high relevance as dimensions and layout may provide highly relevant context to detect a seizure event. The analysis server 130 may identify each object and characteristic of the location included in the contextual information. For each object and characteristic, the analysis server 130 may determine a relevance score and compare the relevance score to a relevance threshold. Those items that satisfy the relevance threshold may be considered relevant and to be included in the virtual environment. As a result of this output, the analysis server 130 may generate the virtual environment (e.g., a three-dimensional rendition of the location).

In generating the virtual environment, the analysis server 130 may provide a further feature in de-identifying the contextual information. The virtual environment may include a blank mask (e.g., a simple wire frame representation) that eliminates any identifying characteristics that may be present that may potentially be used in identifying the patient or the location where the patient is present.

The analysis server 130 may generate contextual motion data through synthesis of the motion information in the virtual environment (step 210). The analysis server 130 may generate a representation of the patient in the virtual environment and simulate the movement exhibited by the patient based on the motion information. Accordingly, with a three-dimensional rendition of the virtual environment, the analysis server 130 may generate a three-dimensional human model actor to perform the movements of the patient where the movements correspond to the movements indicated in the motion information. The model actor of the patient may also provide the further feature in de-identifying the patient. The model actor may include a blank mask (e.g., a simple wire frame representation) that eliminates any identifying characteristics that may potentially be used in identifying the patient. Through the movements of the actor in the virtual environment relative to the surroundings as represented via the contextual information, the analysis server 130 may synthetically generate contextual motion data. Accordingly, the contextual motion data may be motion information that is enriched with contextual information such that the movement of the patient is tracked relative to the surroundings.

Using the contextual motion data, the analysis server 130 may classify the movement of the patient (step 212). In classifying the movement of the patient, the analysis server 130 may utilize the libraries 122 that may have one or more models that learn from historical analyses of contextual motion data and seizure events of the patient and other patients. The models may train a motion classifier where the contextual motion data is fed into the motion classifier to determine whether the movement of the patient is classified as normal or abnormal (e.g., a seizure event or a non-seizure event).

The analysis server 130 may determine whether the movement of the patient is an abnormal motion (decision 214). As a result of the movement of the patient being a normal motion (decision 214, "NO" branch), the analysis server 130 may determine whether the monitoring of the patient has concluded (decision 216). As a result of the monitoring continuing (decision 216, "NO" branch), the analysis server 130 continues to receive sensory data from the EMU 110. As a result of the monitoring concluding (decision 216, "YES" branch), the analysis server 130 may perform subsequent operations as discussed below.

As a result of the movement of the patient being determined to be abnormal (decision 214, "YES" branch), the analysis server 130 may generate an alert (step 218). The analysis server 130 may generate the alert that indicates the registering of the abnormal motion that is provided to one or more targets such as a specialist of the EMU 110, a physician associated with the patient, etc. The analysis server 130 may then determine whether the monitoring of the patient has concluded (decision 216).

As noted above, the method 200 may include further operations that may be performed by the analysis server 130. As described above, the analysis server 130 may be configured to update and/or maintain the libraries 122. With each seizure event in which a seizure may or may not be actually detected, the analysis server 130 may include this seizure event in the libraries 122 where the seizure event includes the contextual motion data associated therewith. The seizure event may also include further information that is received after the seizure event. For example, the further information may be provided by a specialist of the EMU 110, an administrator, a physician, etc. The further information may include a validation of the seizure event as to whether the patient actually experienced a seizure. Further information may be included such as a severity of the seizure, treatment that was provided, etc. With the seizure event included in the libraries 122, the models stored in the libraries 122 may be updated through training techniques such that the models used in the motion classifier may be current with the historical seizure events.

To further illustrate the operations of the analysis server 130, reference is now made to an illustrative exemplary embodiment. According to the illustrative exemplary embodiment, the patient may be located in a hospital room associated with the EMU 110. The hospital room may be equipped with the sensors 112 such that real-world video data is captured from the location. The analysis server 130 may receive and process the real-world video data for scene understanding and context-specific environment generation. The scene understanding may involve generating the contextual information that may include the hospital floor, patient bed, clinical apparatuses, etc. Using a filtering of the contextual information, the analysis server 130 may create a virtual environment representing the location where the patient is present. The scene understanding may also involve generating the motion information that may include human poses, segmentation, movement frequency, velocity, intensity, etc. A model actor may be rendered and placed in the virtual environment where the movement of the patient is simulated based on the motion information. The analysis server 130 may generate the contextual motion data as the patient moves in the hospital room. For example, the patient may experience be moving from the hospital bed toward another area of the hospital room. On the way, the patient may fall and have a seizure. The movement including the change in location and the local changes of the seizure may be captured in the real-world video data and included in the motion information. Thus, in processing the contextual motion data, the motion classifier may determine whether the patient exhibited an abnormal motion. In this instance, the motion classifier may output that an abnormal motion was experienced where previously generated models trained on historical seizure events may provide the foundation in which to generate the output. Subsequent operations may be performed where a specialist of the EMU 110 may validate the seizure event and the contextual motion data may be included in the libraries 122 to further train the models.

The exemplary embodiments are configured to detect a seizure being experienced by a patient through creating and processing of contextual motion data that is motion information enriched with contextual information regarding the surroundings of the location where the patient is present. The exemplary embodiments may receive sensory data that form the basis in generating the motion information and the contextual information. The exemplary embodiments may synthetically generate the contextual motion data through creation of a virtual environment based on the contextual information and rendering a model actor placed in the virtual environment simulating the movements of the patient based on the motion information. The exemplary embodiments may process the contextual motion data to classify the movements of the patient such that an abnormal motion is detected where the abnormal motion may be indicative of a seizure event.

Figure 3:
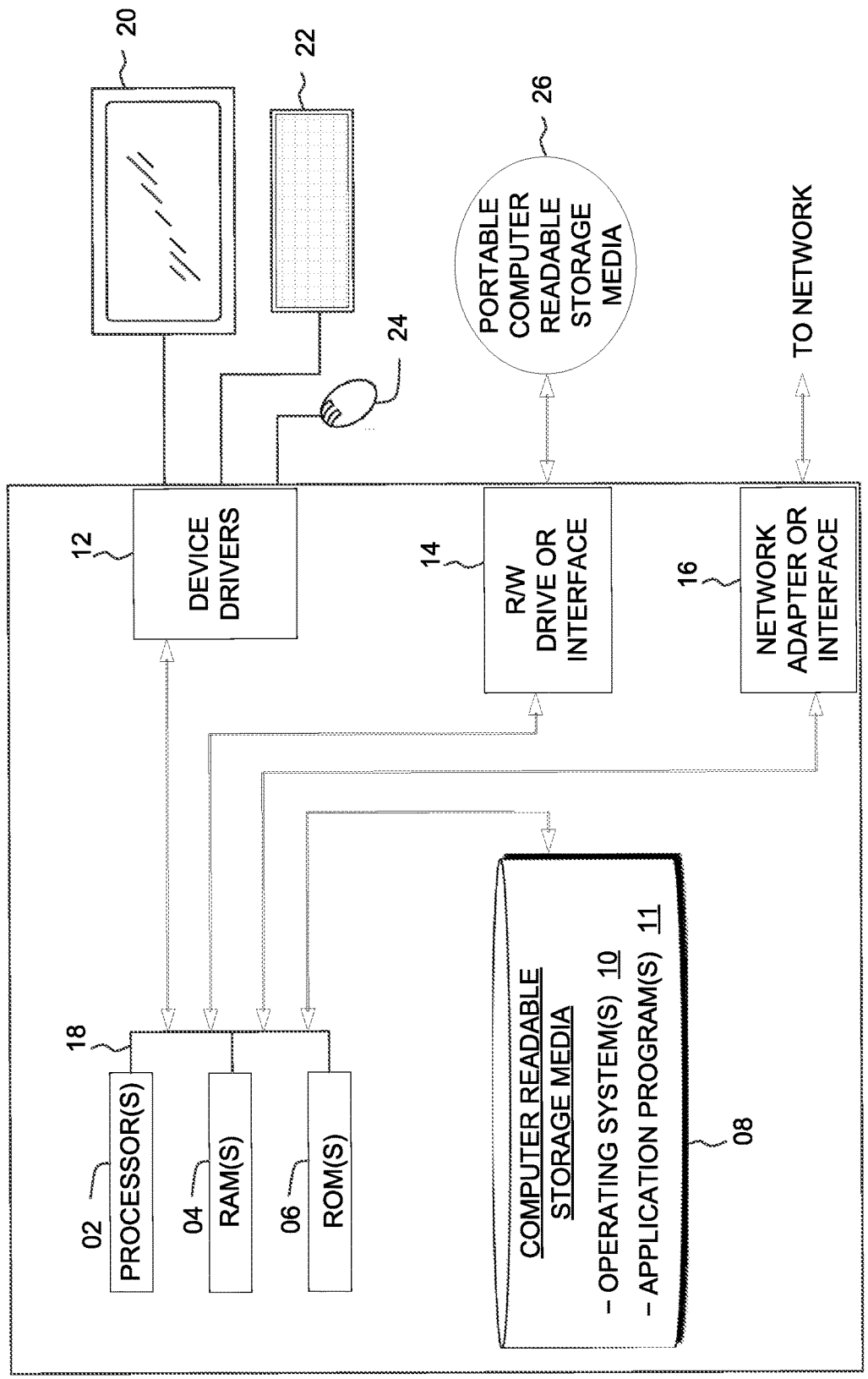
FIG. 3 depicts an exemplary block diagram depicting the hardware components of the motion detection system 100 of FIG. 1, in accordance with the exemplary embodiments.

FIG. 3 depicts a block diagram of devices within the motion detection system 100 of FIG. 1, in accordance with the exemplary embodiments. It should be appreciated that FIG. 3 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
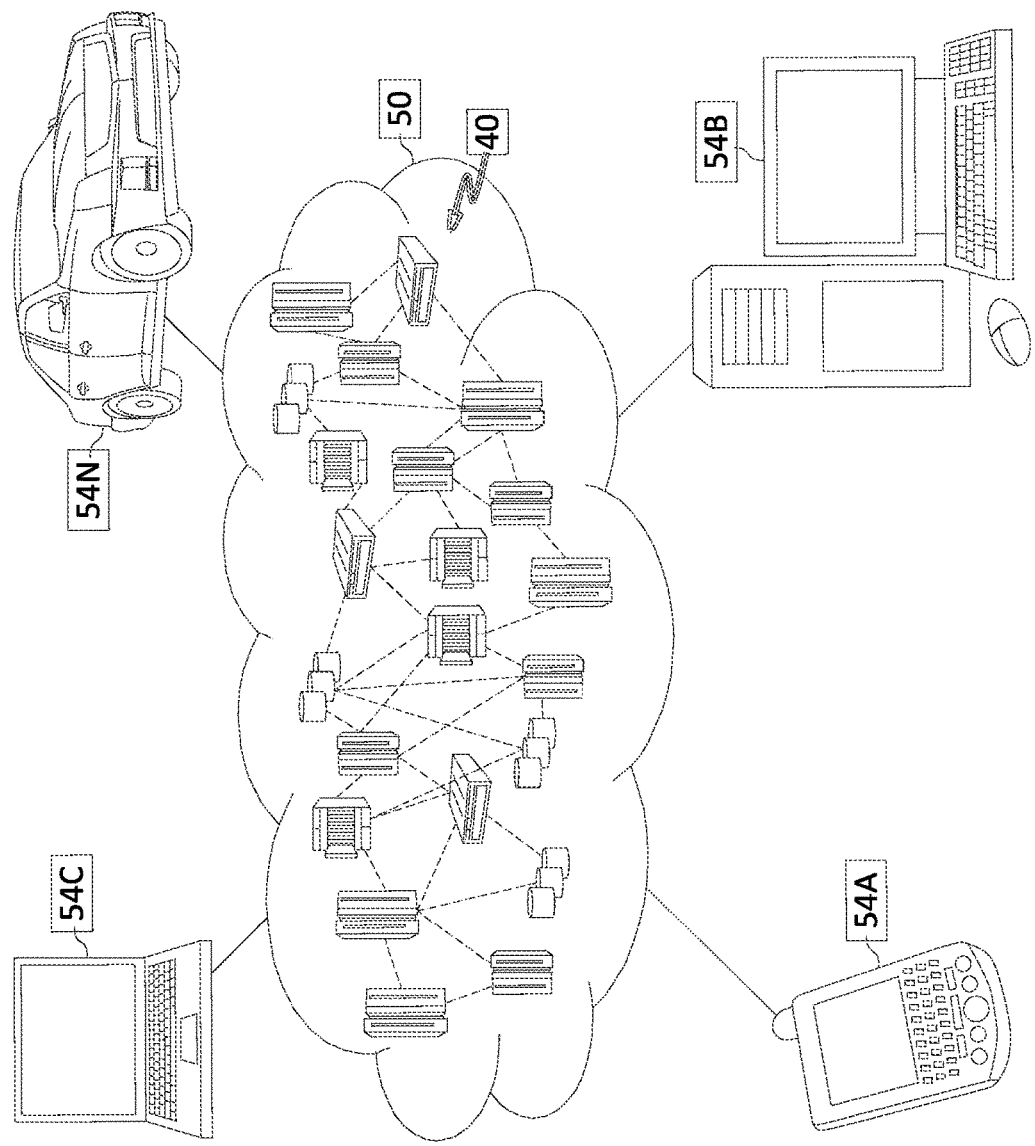
FIG. 4 depicts a cloud computing environment, in accordance with the exemplary embodiments.

Referring now to FIG. 4, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Figure 5:
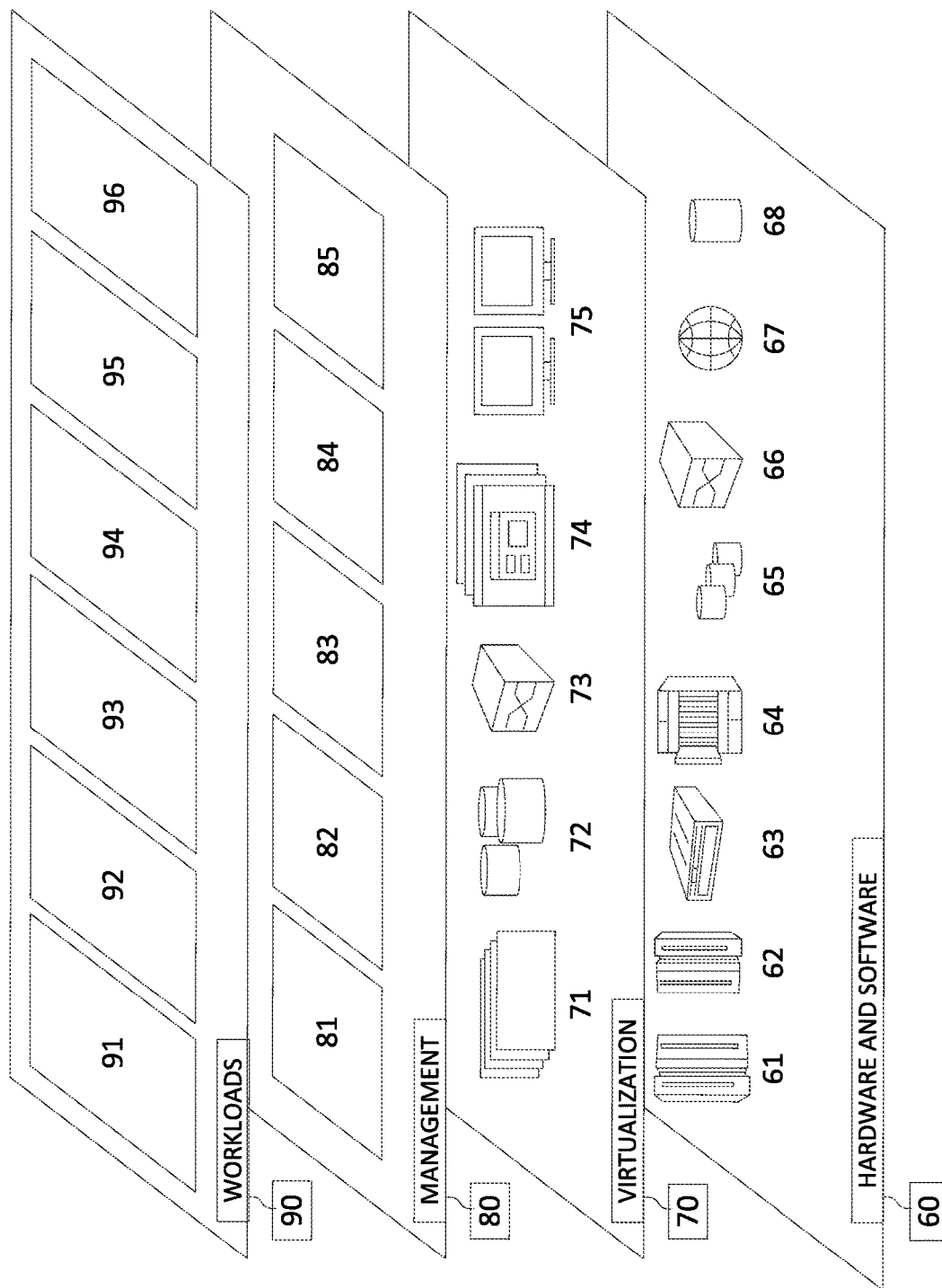
FIG. 5 depicts abstraction model layers, in accordance with the exemplary embodiments.

Referring now to FIG. 5, a set of functional abstraction layers provided by cloud computing environment 50 (FIG. 4) is shown. It should be understood in advance that the components, layers, and functions shown in FIG. 5 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and motion processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for determining abnormal motion from a patient, the method comprising:
    receiving sensory data of the patient and a location in which the patient is present, the sensory data including video data over a period of time the patient is being monitored;
    generating contextual information based on the sensory data, the contextual information indicative of surroundings of the patient and characteristics of the location;
    generating motion information based on the sensory data, the motion information indicative of movement of the patient in the location;
    generating contextual motion data; and
    determining the abnormal motion based on the contextual motion data,
    wherein the contextual motion data is generated by generating a virtual environment based on the contextual information;
    generating a model actor representing the patient;
    generating a simulation of the movement of the patient via the model actor in the virtual environment; and
    processing the simulation.

2. The computer-implemented method of claim 1, wherein the virtual environment and the model actor de-identifies the location and the patient, respectively.

3. The computer-implemented method of claim 1, wherein the abnormal motion is determined according to a model trained with historical seizure events, the historical seizure events including respective historical contextual motion data.

4. The computer-implemented method of claim 3, further comprising:
   validating the abnormal motion; and
   updating the model with the contextual motion data.

5. The computer-implemented method of claim 3, wherein the historical seizure events are from the patient and further patients and from the location and further locations.

6. The computer-implemented method of claim 1, wherein the sensory data further includes electroencephalogram (EEG) data of the patient corresponding to when the movement occurs.

7. A computer program product for determining abnormal motion from a patient, the computer program product comprising:
   one or more non-transitory computer-readable storage media and program instructions stored on the one or more non-transitory computer-readable storage media capable of performing a method, the method comprising:
      receiving sensory data of the patient and a location in which the patient is present, the sensory data including video data over a period of time the patient is being monitored;
      generating contextual information based on the sensory data, the contextual information indicative of surroundings of the patient and characteristics of the location;
      generating motion information based on the sensory data, the motion information indicative of movement of the patient in the location;
      generating contextual motion data; and
      determining the abnormal motion based on the contextual motion data,
      wherein the contextual motion data is generated by generating a virtual environment based on the contextual information based;
      generating a model actor representing the patient;
      generating a simulation of the movement of the patient via the model actor in the virtual environment; and
      processing the simulation.

8. The computer program product of claim 7, wherein the virtual environment and the model actor de-identifies the location and the patient, respectively.

9. The computer program product of claim 7, wherein the abnormal motion is determined according to a model trained with historical seizure events, the historical seizure events including respective historical contextual motion data.

10. The computer program product of claim 9, wherein the method further comprises:
    validating the abnormal motion; and
    updating the model with the contextual motion data.

11. The computer program product of claim 9, wherein the historical seizure events are from the patient and further patients and from the location and further locations.

12. The computer program product of claim 7, wherein the sensory data further includes electroencephalogram (EEG) data of the patient corresponding to when the movement occurs.

13. A computer system for determining abnormal motion from a patient, the computer system comprising:
    one or more computer processors, one or more non-transitory computer-readable storage media, and program instructions stored on the one or more of the computer-readable storage media for execution by at least one of the one or more processors capable of performing a method, the method comprising:
       receiving sensory data of the patient and a location in which the patient is present, the sensory data including video data over a period of time the patient is being monitored;
       generating contextual information based on the sensory data, the contextual information indicative of surroundings of the patient and characteristics of the location;
       generating motion information based on the sensory data, the motion information indicative of movement of the patient in the location;
       generating contextual motion data; and
       determining the abnormal motion based on the contextual motion data,
       wherein the contextual motion data is generated by generating a virtual environment based on the contextual information;
       generating a model actor representing the patient;
       generating a simulation of the movement of the patient via the model actor in the virtual environment; and
       processing the simulation.

14. The computer system of claim 13, wherein the virtual environment and the model actor de-identifies the location and the patient, respectively.

15. The computer system of claim 13, wherein the abnormal motion is determined according to a model trained with historical seizure events, the historical seizure events including respective historical contextual motion data.

16. The computer system of claim 15, wherein the method further comprises:
    validating the abnormal motion; and
    updating the model with the contextual motion data.

17. The computer system of claim 15, wherein the historical seizure events are from the patient and further patients and from the location and further locations.

* * * * *